United States Patent [19]

Awerbuch

[11] 4,352,880
[45] Oct. 5, 1982

[54] DIFFUSION BIOASSAY FOR THE QUANTITATIVE DETERMINATION OF MUTAGENICITY

[75] Inventor: Tamara E. Awerbuch, Cambridge, Mass.

[73] Assignee: Massachusetts Institute of Technology, Cambridge, Mass.

[21] Appl. No.: 76,199

[22] Filed: Sep. 17, 1979

[51] Int. Cl.$^3$ .............................................. C12Q 1/68
[52] U.S. Cl. .......................................... 435/6; 435/29; 435/32; 435/240
[58] Field of Search ....................... 435/6, 29, 32, 172, 435/240, 241, 810

[56] References Cited

U.S. PATENT DOCUMENTS

| | | | |
|---|---|---|---|
| 3,493,772 | 2/1970 | Daughters et al. | 435/39 |
| 3,819,490 | 6/1974 | Klingstrom et al. | 435/32 |
| 4,066,510 | 1/1978 | Thilly | 435/29 |

FOREIGN PATENT DOCUMENTS 774155  5/1957  United Kingdom .................. 435/29

OTHER PUBLICATIONS

Ames, "Identifying Envir. Chemicals Causing Mutations & Cancer," *Science*, vol. 204, May 11, 1979, pp. 587-593.

Ames et al., "Does Carcinogenic Potency Correlate with Mutagenic Potency in the Ames Assay," *Nature*, vol. 274, Jul. 6, 1978, pp. 19 and 20.

Ames et al., "Methods for Detecting Carcinogens & Mutagens with the Salmonella/Mammalian-Microsome Mutagenicity Test," *Mutation Research*, 1975, pp. 347-364.

Devoret, "Bacterial Tests for Potential Carcinogens," *Scientific American*, Aug. 1979, pp. 40-49.

Hewitt, *Microbiological Bioassay*, Academic Press, New York, 1977.

Primary Examiner—Peter A. Hruskoci
Attorney, Agent, or Firm—Arthur A. Smith, Jr.; David E. Brook

[57] ABSTRACT

A quantitative bioassay employing the well known diffusion bioassay is described herein. The bioassay allows the calculation of the minimum concentration of a test agent which produces mutation in a tester strain of cells employed in the diffusion bioassay. A novel method for determining the stability of the agent tested in the test environment is also described.

6 Claims, 13 Drawing Figures

DIFFUSION BIOASSAY FOR THE QUANTITATIVE DETERMINATION OF MUTAGENICITY

TECHNICAL FIELD

This invention is in the field of biochemistry and more specifically relates to genetic toxicology.

BACKGROUND ART

Compounds or other agents which can chemically alter the DNA of a cell are capable of inducing genetic diseases such as Lesch-Nyhan syndrome, hemophilia, sickle cell anemia, and cystic fibrosis. Compounds or agents which have this potential are known as mutagens. Many mutagens have also been found to have the capability of inducing cancer in test animals or human beings, and are thus also carcinogens. It is clearly desirable, therefore, to have methods for determining the potential mutagenicity of such compounds or agents in a practical, efficient and inexpensive manner.

Bacterial mutation assays have been proposed for this purpose. One of the most commonly employed bacterial assays for mutagenicity is known as the Ames assay and employs a set of *Salmonella typhimurium* strains which are permeable to a wide range of chemicals and also are partially deficient in DNA repair. Ames, B. N., McCann, J. and Yamasaki, E., *Mutation Research*, 31, 347-379 (1975). In this system, a chemical's mutagenicity is determined by its ability to revert a set of histidine-requiring mutants of *S. typhimurium* back to histidine prototrofy through reverse mutation of the original DNA lesion or through a second site mutation.

A more recent assay which employs diploid human lymphoid blastoid cell lines has been developed. This assay depends upon the expression of phenotypic resistance to 6-thioguanine or other purines which serve as substrates for hypoxanthine guaninine phosphoribosyl transferase. This assay is described in U.S. Pat. No. 4,066,510 issued to William G. Thilly.

Although assays of the type described above have proven to be reliable, they do involve extensive experiments of cell cultures at various concentrations of mutagen in order to produce meaningful data. Additionally, they do not predict, with high reliability, the minimum concentration of tested mutagent at which mutagenicity occurs.

Another common biological tool is the diffusion bioassay. In such diffusion bioassays, the reaction of bacteria plated on an agar nutrient medium to an added chemical substance is determined. The chemical diffuses outwardly from some initial spot (e.g., the center of the petri dish), and after a certain incubation period, one or concentric rings around the center can be observed which mark areas in which the bacteria have been affected by the chemical. Such systems have been used in a qualitative manner to determine mutagenicity, and an example of such a test has become known as the Ames spot test. See Ames et al., Ibid. Diffusion bioassays have also been employed to determine the potency of an antibiotic by comparing the radius of a sample of unknown potency to the radius of a standard reference. See Hewitt, W., *Microbiological Bioassay*, Academic Press, New York, 1977.

Disclosure of the Invention

This invention relates to an assay for determining the mutagenic effect of a test agent. In one embodiment, a diffusion bioassay for chemical substances is employed and an equation is used to express the effective time-integrated concentration distribution of the diffusing test substance. This assay permits the lowest concentration at which the test agent produces mutagenicity to be determined simply from a knowledge of the radius of the mutagenic zone formed in the bioassay. In the case of chemical substances, this is determined employing the diffusion coefficient for the compound tested and the half-lifetime of the mutagen. In most cases, the half-lifetime of the mutagen can be determined directly from the experimental data obtained from the diffusion bioassay.

This new bioassay allows a threshold concentration for the test agent to be determined which is significantly different from zero. Additionally, the bioassay is highly reliable, relatively quick to perform, and relatively inexpensive compared to prior methods. These results flow from the fact that a wide range of concentrations of the mutagen is present in one cell culture plate. Thus, the requirement of running a series of plates at different concentrations is obviated.

BEST MODE OF CARRYING OUT THE INVENTION

The invention will now be more specifically described with particular reference to the Figures and to examples.

Figure 1:
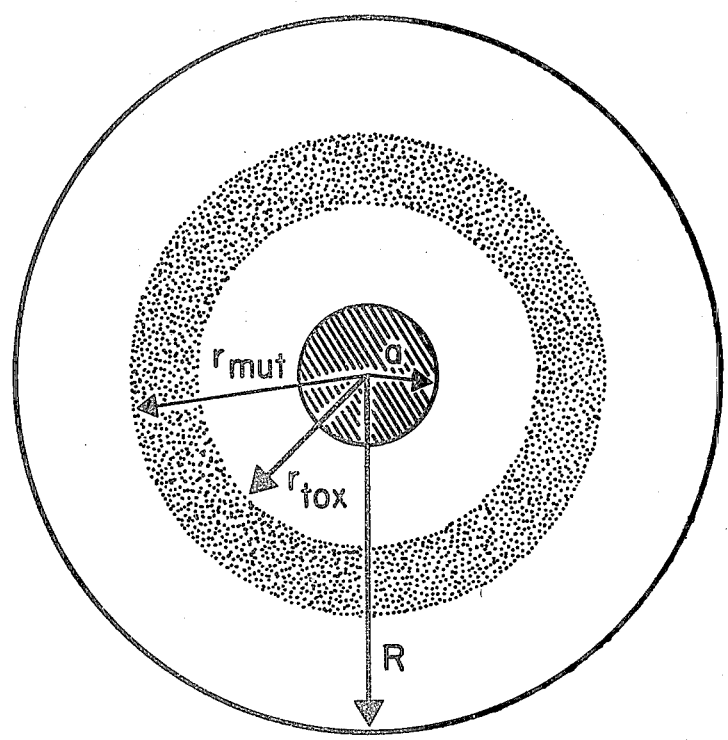
FIG. 1 is a schematic representation of a diffusion bioassay.
Figure 2:
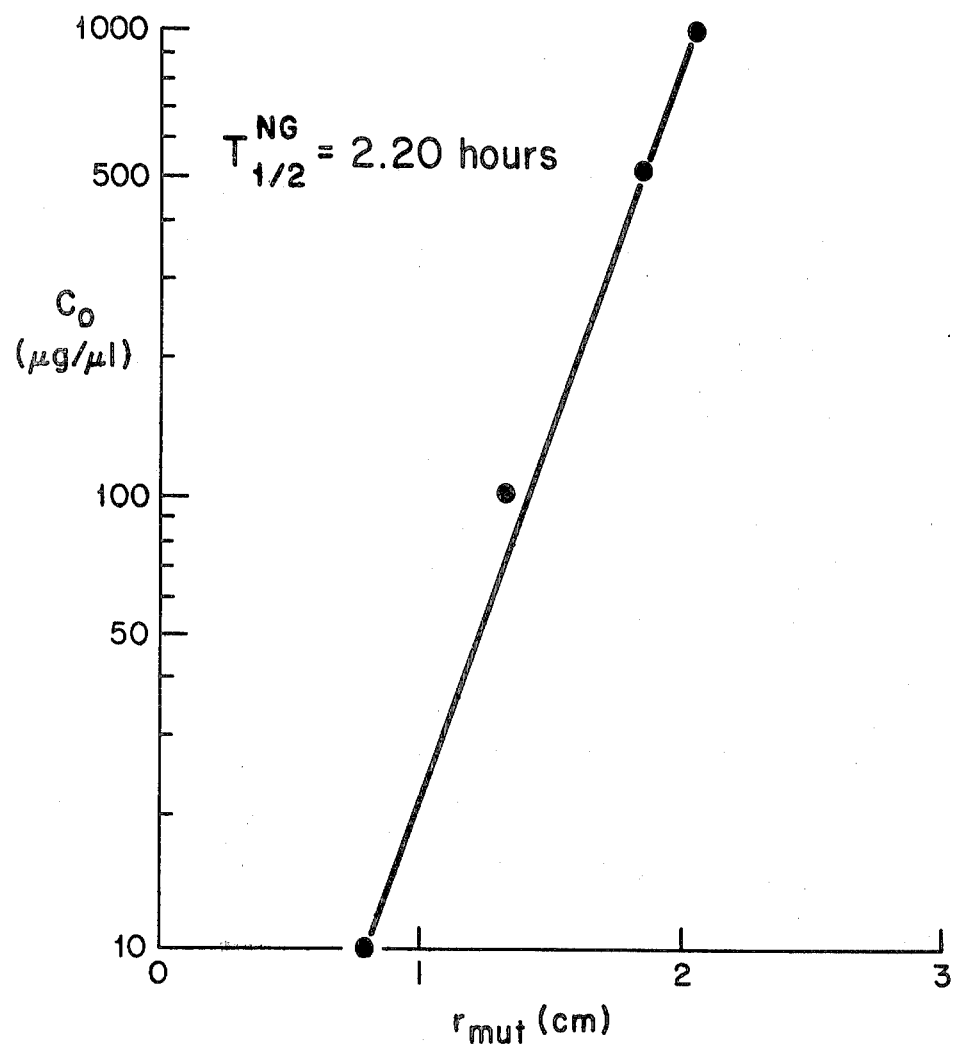
FIGS. 2-7 are plots of the logarithm of the initial concentration of test compounds versus the radius of the mutagenic zone formed.
Figure 3:
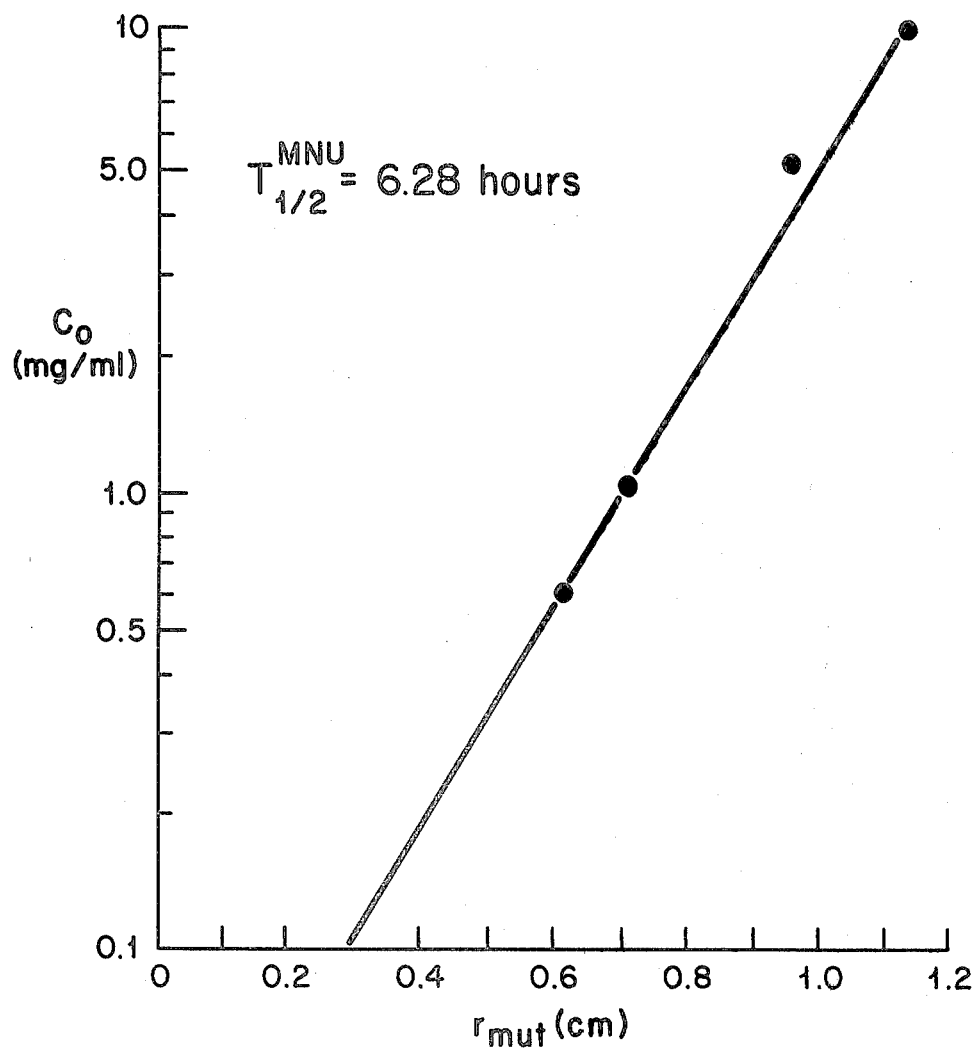
Figure 4:
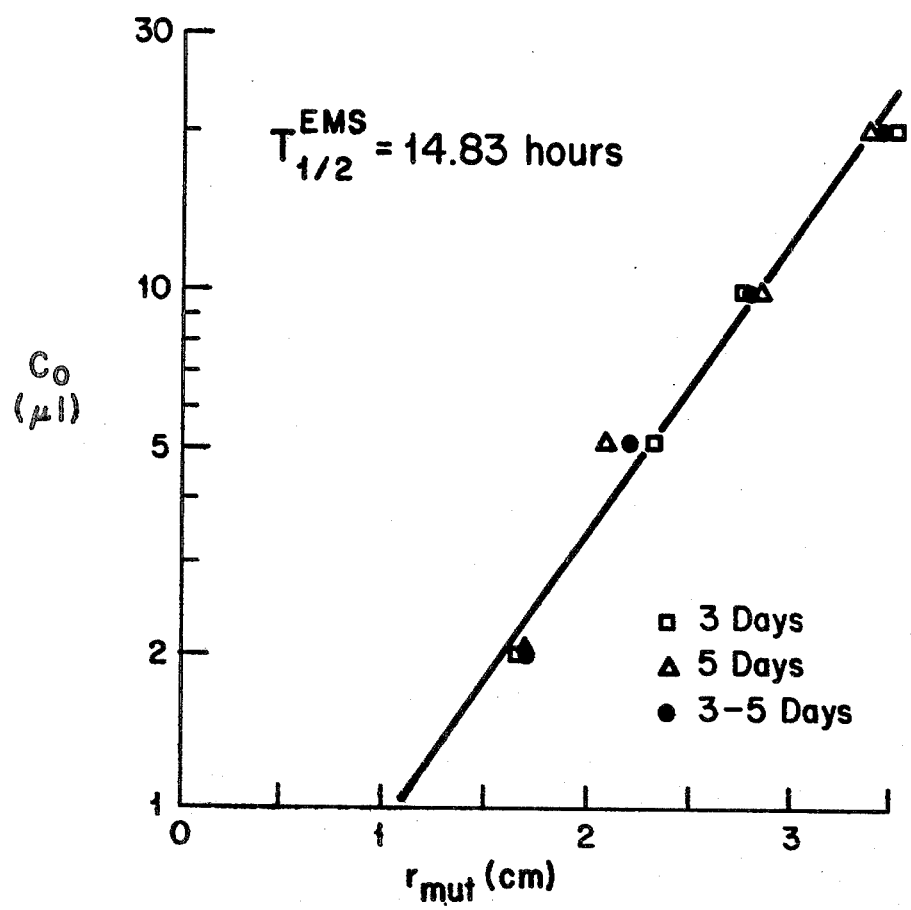
Figure 5:
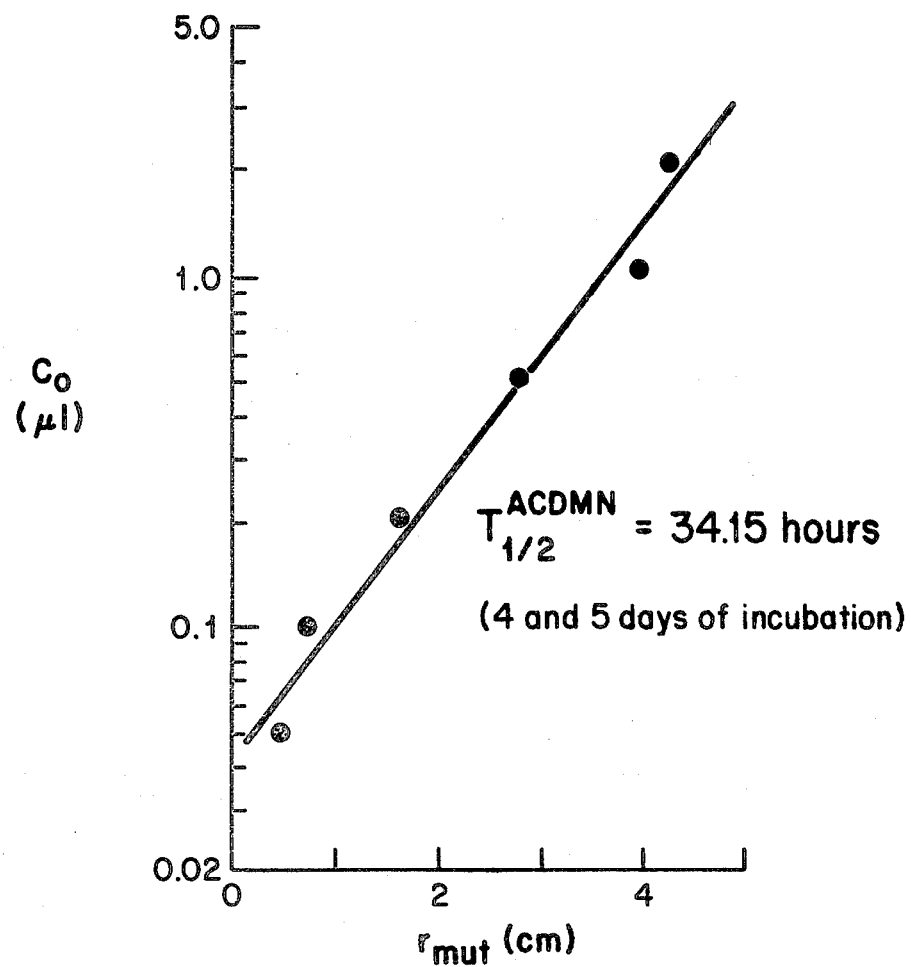
Figure 6:
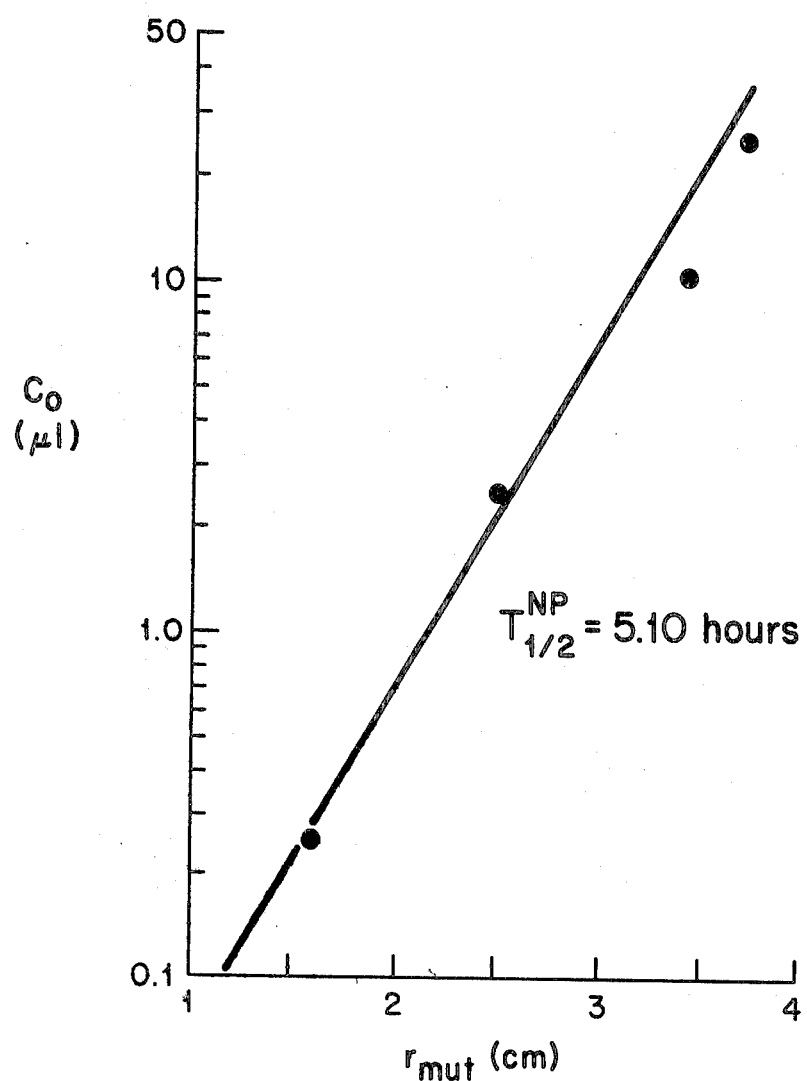

A schematic representation of a diffusion bioassay is presented in FIG. 1. In such an assay, bacteria are placed in a suitable medium, such as agar, to form a bacterial lawn. A known quantity of the test substance is then placed on a piece of filter paper located at the center of the culture dish and having a radius a. After a few days of incubation, the ring-shaped pattern illustrated in FIG. 1 is observed. In the inner region, where the radius is greater than the radius of the filter paper but less than the toxic radius, $r_{tox}$, the bacteria are killed due to the high concentration of the mutagenic substance. In the next concentric region formed between $r_{tox}$ and the mutagenic radius, $r_{mut}$, viable mutants are produced, while at larger distances ($r > r_{mut}$) no mutants are detected, presumably due to the fact that the concentration of the mutagenic agent is too low.

A mathematical model of this system was constructed taking into account the physical-chemical properties of a chemical mutagen, such as its solubility in solution and its stability in the medium, as well as the response of the bacteria to the physical-chemical changes of the system. The major assumption in this model was that the appearance of mutated bacteria was governed exclusively by the local-temporal concentration c(r,t) of the diffusing mutagen, that satisfies a simple, two-dimensional diffusion equation, described by the change of concentration with time for each point in the culture, as follows:

$$\frac{\delta c}{\delta t} = D\left(\frac{\delta^2 c}{\delta r^2} + \frac{1}{r}\frac{\delta c}{\delta r}\right) - \frac{c}{\tau} \quad \text{(I)}$$

In this equation, r is the distance from the center of the culture dish, t is the time starting from the moment of introduction of the mutagen, D is the diffusion constant of the mutagen, and $\tau$ is the decay time or half-lifetime of the mutagen divided by ln 2. Other physicalchemical factors, such as the pH and temperature, were taken into account only insofar as they affected c(r,t) through the quantities D and $\tau$. Factors of a microbiological nature, such as the effect of the membrane permeability of the bacteria to the mutagent on c(r,t) were ignored. The justification for treating the diffusive transport of the chemical as a two-dimensional rather than as a three-dimensional process is the small height-to-width ratio of the agar gel employed.

The two-dimensional diffusion equation (I) was solved with the following initial and boundary conditions:

$$c(r, t = 0) = \begin{cases} c_o \text{ for } r < a \\ 0 \text{ for } r > a \end{cases} \quad (1)$$

where a is the radius of the filter paper and $c_o$ is the initial surface density of the mutagenic substance (i.e., $\tau a^2 c_o$ is the total weight of the mutagen); and $$\frac{\delta c}{\delta r}(r = R, t) = 0 \quad (2)$$

where R is the radius of the petri dish. This condition ensures that there is now flow of the mutagen out of the petri dish.

The solution employing material from Carslaw, H. S. and Jaeger, J. C., *Conduction of Heat in Solids,* Clarenden Press, Oxford, 204(1959), is:

$$c(r,t) = c_o \exp(-t/\tau)\left\{(a/R)^2 + 2(a/R)\sum_{n=1}^{\infty} \exp(-D\alpha_n^2 t/R^2) J_o(r\alpha_n/R) J_1(a\alpha_n/R)[\alpha_n J_o^2(\alpha_n)]\right\} \quad \text{(II)}$$

where $J_o$ and $J_1$ are the cylindrical Bessel functions of order zero and one, respectively, and $\alpha_n$ are the roots of the equation $J_1(\alpha) = 0$. with the aid of a computer, equation (II) was integrated to find how the cumulative concentration averaged with time varied at various points of the petri dish. Much of the data actually obtained is presented in the Examples given herein.

Tester strains actually employed in the experimental work described were bacterial strains *S. typhimurium* TA1535 and *S. typhimuirum* TA100. Nevertheless, other bacterial or human cell and tester strains could also be used with the assay described herein.

Once the mutagenic zone is formed in the culture, the distance to the outer boundary of the zone is determined and taken as $r_{mut}$. This can be measured by placing the culture over calibrated paper, such as graph paper or by other measuring techniques.

In regard to agents to be tested, it is believed that any substance or agent can be employed. For those which are at least partially water soluble, there should be a way to measure the half-lifetime $\tau_{\frac{1}{2}}$. In most cases, the latter requirement can be achieved from the data obtained in the bioassay, as explained herein. In other cases, the half-lifetime can be determined by other analytical procedures such as spectrophotometry.

Radioactive substances, such as colbalt 60, rubidium 86 and sodium 24, can also be employed. It might be preferable with these to place the radioactive substance in a well at the center of the culture. Agents such as U.V. light can also be employed by exposing the culture to varying intensities at different radii.

Diffusion coefficients for soluble substances also need to be established or obtained from the literature. At low agar concentrations, diffusion constants of low molecular weight chemicals can be assumed to be the same as in water. An empirical relationship exists between the diffusion coefficient, D, and the molecular weight, M, at a fixed temperature for small molecules. This equation is $DM^{\frac{1}{2}} = $ a constant. Thus, by knowing the values of D and M for one substance, such as glucose, and the molecular weight for the agent tested, its diffusion coefficient can be determined. For more complicated compounds, the diffusion coefficient can be established by similar procedures.

The mathematical treatment of the model for the diffusion bioassay resulted in a finding that there was a linear relationship between the logarithm of the initial concentration of the mutagen on the filter paper and the size of the mutagenic zone, as follows:

$$\ln c_o \approx r_{mut}/\sqrt{D\tau} + \text{constant}.$$

The slope of this plot, $1/\sqrt{D\tau}$ allowed the decay time to be established from the diffusion experiment without having to determine it in a separate set of experiments. This is illustrated specifically in the examples which follow.

EXAMPLE 1

Four known carcinogens and two known procarcinogens, which act through base-pair substitutions, were employed. The four known carcinogens were N-Methyl-N'-nitro-N-nitrosoguanidine (NG), ethyl-methane-sulfonate (EMS), N-Methyl-N-nitrosourea (MNU), Acetoxydimethylnitrosoamine (AcDMN), and the two procarcinogens were nitrosopyrrolidine (NP) and N-nitrosomorpholine (NM). NG and MNU were obtained in crystalline form and dissolved in absolute alcohol to give stable stock solutions of 1 mg/ml and 10 mg/ml. Because of instability problems, each desired concentration of carcinogen was specially prepared by dissolving aliquots of these stock solutions, and of AcDMN and EMS, which are liquids, in a phosphate buffer (pH=7.0) and immediately used. NM and NP are stable in an aqueous environment and stock solutions were prepared by directly dissolving these in phosphate buffer (pH=7.0).

The bacterial tester strains employed were *S. typhimurium* TA1535 and *S. typhimurium* TA100. All cells were in the late log phase.

Minimal medium plates were prepared by adding 5 ml and 25 ml of media containing 0.6% agar, 0.6% NaCL salts to 60 mm and 10 mm Falcon petri dishes, respectively. Lawns of *S. typhimurium* TA1535 or TA100 were prepared as described by Ames et al., *Mutation Research,* 31, 347–79 (1975): Thus, a mixture of 2 ml molten top agar (0.6% agar, 0.5% NaCl) containing 0.05 mM histidine and 0.05 mM biotin, which were freshly added, and 0.2 ml of the bacterial suspension at a concentration of $2.5 \times 10^9$/ml was poured on minimal medium plates.

The preparation of bacterial cultures for the diffusion bioassays was carried out by starting with overnight cultures prepared in nutrient broth. Then, 0.2 ml of the cultures were transferred to 50 ml of fresh nutrient medium and incubated for 8 hours in a shaker at 37° C. This solution served as a stock for the diffusion bioassays.

0.025 ml of a solution containing a known concentration of the mutagenic chemical was absorbed on a 6.35 mm filter paper disk. The concentrations for NG were 1000, 500, 100 and 10 μg/ml, respectively. 10, 1, 0.5 and 0.1 mg/ml were used for MNU. Aliquots of 2, 5, 10 and 20 mls of EMS were used to be placed on the filter paper and equivalents of 2, 1, 0.5, 0.2, 0.1 and 0.05 ml were employed for AcDMN. The filter paper was then placed in the center of the solidified agar containing the bacteria. After a few days of incubation at 37° C., the radii of the different zones were measured.

The procarcinogens NM and NP were employed in essentially the same manner except that microsomalactivation was achieved by adding 0.5 ml of an activating mixture with the 0.2 ml of bacterial culture. This activating mixture contained, per ml: 8 μMoles $MgCl_2$, 33 μMoles KCl, 5 μMoles, Glu-G-P, 4 μMoles NADP, 100 μMoles sodium phosphate, pH=7.4, and 0.1 ml of rat liver homogenate fraction s-9 obtained from Litton Bionetics. The aliquots tested were 25 μl of the original solution and dilutions of 1:10 and 1:100. For NP, an additional dilution of 1:2 was tested.

For purposes of comparison, homogeneous bioassays were performed in a similar fashion to the diffusion bioassays except that the bacteria were treated with a given concentration of the mutagen which was homogeneously distributed throughout the petri dish. 0.2 ml of the solutions containing the various concentrations of the mutagen were added to the top molten agar layer together with 0.2 ml of the bacterial suspension and the mixture was poured on the minimal medium plate as previously described. Active mutagens brought about appearance of revertants on the background of the lawn after a few days of incubation at 37° C. Microsomal activation mixtures were added to the procarcinogens tested, as previously described.

All the straight lines of best fit for the experimental data were obtained by regression analysis. t-tests for the comparison of half lifetimes obtained by different experimental methods were done according to the method that gives a weighted average estimate of the standard deviation.

In order to determine whether the potencies obtained by the diffusion method for the different mutagens are significantly different, an F test for the analysis of variance was performed. For this purpose program BMD0IV from the book *Biomedical Computer Programs* was used. Dixon, W. J., *BMD—Biomedical Computer Programs,* University of California Press, Berkeley, Los Angeles, London (1974).

The experimentally determined values of $r_{mut}$ corresponding to different initial concentrations ($C_o$) for NG, MNU, EMS, AcDMN, NP and NM are presented in Tables 1-6, respectively.

TABLE 1

Radius of Mutagenic Zone Formed by Different Concentrations of NG

| $c_o$(mg/ml) | $r_{mut}$(cm)* |
|---|---|
| 1 | 2.22 ± 0.05 |
| 0.5 | 1.98 ± 0.02 |
| 0.1 | 1.55 ± 0.04 |
| 0.01 | 0.88 ± 0.05 |
| 0 | 0 |

*$r_{mut}$ are means of 18 measurement of experiments
Size of Petri Dish: R = 2.5 cm
Strain: *S. typhimurium* TA 1535
Incubation Time: 2½ days
$\tau_{\frac{1}{2}}$ = 2.20 hrs.

TABLE 2

Radius of Mutagenic Zone Formed by Different Concentrations of MNU

| $c_o$(mg/ml) | $r_{mut}$(cm)* |
|---|---|
| 10 | 1.12 ± 0.08 |
| 5 | 0.95 ± 0.09 |
| 1 | 0.71 ± 0.04 |
| 0.5 | 0.62 ± 0.06 |
| 0 | 0 |

*$r_{mut}$ are means of 16 measurements of experiments
Size of Petri Dish: R = 4.25 cm
Strain: *S. typhimurium* TA 1535
Incubation time: 2½ days
$\tau_{\frac{1}{2}}$ 0.628 hrs.

TABLE 3

Radius of Mutagenic Zone Formed by Different Concentrations of EMS after Different Incubation Times

| $c_o$ μl/disc | $r_{mut}$(cm) after incubation of 1½ days | $r_{mut}$(cm) 2½ days | $r_{mut}$(cm) 3 days | $r_{mut}$(cm) 5 days | Average $r_{mut}$(cm) 3-5 days |
|---|---|---|---|---|---|
| 20 | ~ | 2.78 ± 0.07 | 3.4 ± 0.08 | 3.52 ± 0.24 | 3.45 ± 0.16 |
| 10 | 1.98 ± 0.09 | 2.27 ± 0.05 | 2.83 ± 0.06 | 2.78 ± 0.09 | 2.79 ± 0.07 |
| 5 | 1.63 ± 0.12 | 1.9 ± 0.0 | 2.07 ± 0.09 | 2.31 ± 0.12 | 2.19 ± 0.11 |
| 2 | 1.26 ± 0.12 | 1.31 ± 0.08 | 1.7 ± 0.07 | 1.7 ± 0.1 | 1.7 ± 0.08 |
| 0 | 0 | 0 | 0 | 0 | 0 |
| $\tau_{\frac{1}{2}}$ | 4.83 hrs. | 9.76 hrs. | pooled | ⟶ | 14.83 hrs. |
| N (number of measurements) | 6 | 6 | 6 | 6 | 12 |

Size of Petri Dish: R = 4.25 cm
Strain: *S. typhimurium* TA 1535

TABLE 4

Radius of Mutagenic Zone Formed by Different Concentrations of AcDMN After 2.5 and 4–5 Days of Incubation

| $c_o$(μl/disc) | $r_{mut}$(cm) 2.5 days | $r_{mut}$(cm) 4 and 5 days |
|---|---|---|
| 2 | 3.14 ± 0.10 | 4.25 ± 0.00 |
| 1 | 2.67 ± 0.04 | 3.98 ± 0.16 |
| 0.5 | 1.93 ± 0.04 | 2.81 ± 0.14 |
| 0.2 | 1.21 ± 0.6 | 1.66 ± 0.33 |
| 0.1 | 0.75 ± 0.04 | 0.75 ± 0.41 |
| 0 | 0.47 ± 0.09 | 0.47 ± 0.09 |
| correlation coefficient | 0.904 | 0.988 |
| $\tau_{\frac{1}{2}}$ | 19.15 hrs. | 34.5 hrs. |
| N (Number of Measurements) | 6 | 6 |

Size of Petri Dish: R = 4.25 cm
Strain: *S. typhimurium* TA 1535

TABLE 5

Radius of Mutagenic Zone Formed by Different Concentrations of NP

| Co μl/disc | $r_{mut}$(cm)* |
|---|---|
| 0.25 | 1.6 ± 0.18 |
| 2.5 | 2.5 ± 0.28 |
| 10 | 3.43 ± 0.32 |
| 25 | 3.7 ± 0.31 |

*$r_{mut}$ are means of 6 measurements.
Size of Petri Dish: 4.25 cm
Incubation Time: 3 days
$\tau_{\frac{1}{2}} = 5.10$ hrs

TABLE 6

Radius of Mutagenic Zone Formed by Different Concentrations of NM

| Co μl/disc | $r_{mut}$(cm)* |
|---|---|
| 0.25 | 1.31 ± 0.12 |
| 2.5 | 2.25 ± 0.12 |
| 25 | 3.6 ± 0.12 |

*$r_{mut}$ are means of 6 measurements.
Size of Petri Dishes: R = 4.25
Strain: *S. typhimurium* TA 1535
$\tau_{\frac{1}{2}} = 6.00$ hrs The half lifetimes of the four mutagens ($\tau_{\frac{1}{2}}$) were obtained by both spectrophotometrical studies and by data derived from the reversion bioassays employing *S. typhimurium* TA1535.

In the spectrophotometrical techniques, the desired concentrations were made by dissolving 0.05 ml of a stock alcoholic solution of 10 mg/ml of NG or MNU or 0.1 ml of EMS or AcDMN in a mixture containing 5 ml minimal medium, 2 ml of a 0.5% solution of NaCl, 0.025 ml phosphate buffer solution (pH=7.0) and 0.2 ml of bacterial nutrient medium. This was done since the stability of the carcinogens in aqueous media was recognized to depend very much on the composition of the solution, and was very sensitive to pH and added solutes. Agar was omitted in order to facilitate spectroscopic investigation of the solution, and it was assumed that agar gel did not influence the lifetimes of the carcinogens. The optical absorption of the solutions was measured at different time intervals with a Beckman Model 25 spectrophotometer at the characteristic absorbence wavelength of the different carcinogens, which are:

$\lambda_{NG} = 400$ mμ, $\lambda_{MNU} = 390$ mμ, $\lambda_{EMS} = 266$ μm, $\lambda_{AcDMN} = 337$ mμ.

Between measuring times the solutions were kept at 37° C.

Values for the half-lifetimes ($\tau_{\frac{1}{2}}$) for the four direct carcinogens were then obtained by plotting the logarithm of absorbance at the characteristic wavelength for each compound versus time. These plots represented the disappearance of the carcinogen in their pertinent environment as measured spectrophotometrically. Each plot yielded a straight line indicating that the decay was of a first order nature. From the plots, the half-lifetimes obtained were:

$\tau_{\frac{1}{2}}^{NG} = 2.25$ hrs, $\tau_{\frac{1}{2}}^{MNU} = 0.59$ hrs, $\pi_{\frac{1}{2}}^{EMS} = 13.8$ hrs $\tau^{ACDMN} = 30.4$ hrs $\tau_{\frac{1}{2}}$ was also derived from the diffusion bioassays. Plots of the natural logarithm of the original chemical dose (1 n $C_o$) versus the radius of the mutagenic zone ($r_{mut}$) gave a straight line for each of the chemical studies, as seen in FIGS. 2–7.

For NG, MNU, NM and NP, 2½ days of incubation at 37° C. were required to stabilize the measured radius at which mutagenicity is observed ($C_{mut}$). 3 and 4 days incubation at 37° C. were required, respectively, for EMS and AcDMN.

The values of $\tau_{\frac{1}{2}}$ for NG, MNU, EMS and AcDMN obtained from spectroscopical measurements were in agreement with values of $\tau_{\frac{1}{2}}$ obtained from the slope of the plot of 1 n $C_o$ vs. $r_{mut}$.

The values of $\tau_{\frac{1}{2}}$ obtained spectrophotometrically and those obtained parametrically from the experiments on plates are summarized for comparative purposes in Table 7. A t-test at $\alpha=0.05$ showed no difference between the values of $\tau_{\frac{1}{2}}$ obtained by the two methods.

TABLE 7

| | $\tau_{\frac{1}{2}}$ Spectroscopically | $\tau_{\frac{1}{2}}$ Parametrically |
|---|---|---|
| NG | 2.25 hrs | 2.20 hrs |
| MNU | 0.599 hrs | 0.628 hrs |
| EMS | 13.79 hrs | 14.83 hrs |
| AcDMN | 30.4 hrs | 34.15 hrs |

The results of the reversion assay using *S. typhimurium* TA100 as the tester strain and NG as the experimental chemical are presented in Table 8. Essentially the same size of mutagenic zones resulted for a given concentration of chemical placed at the center of the petri dish as for the bioassays with NG and *S. typhimurium* TA1535. Thus, the same calculated $\tau_{\frac{1}{2}}$ lifetime: $\tau_{\frac{1}{2}}^{NG}=2.20$ hours was obtained.

TABLE 8

Mutagenic Radius Zone Formed by Different Concentrations of NG

| $c_o$(mg/ml) | $r_{mut}$(cm)* |
|---|---|
| 1 | 2.16 ± 0.05 |
| 0.5 | 1.95 ± 0.02 |
| 0.1 | 1.57 ± 0.06 |
| 0.01 | 0.92 ± 0.05 |

TABLE 8-continued

Mutagenic Radius Zone Formed by Different Concentrations of NG

| $c_o$(mg/ml) | $r_{mut}$(cm)* |
|---|---|
| 0 | 0 |

*$r_{mut}$ are means of 6 measurements.
Size of Petri Dish: 2.5 cm
Strain: S. typhimurin TA 100
Incubation Time: 2½ days
$\tau_{\frac{1}{2}}$ = 2.2 hrs Diffusion coefficients for the mutagens tested were calculated using the formula $DM^{\frac{1}{3}}$ = constant and known data for glucose. The results were:

| Molecular weight | | Diffusion coefficient | |
|---|---|---|---|
| $M_{NG}$ | = 147 | $D_{NG}$ | = 7.2 × 10⁻⁶cm²/sec |
| $M_{MNU}$ | = 103 | $D_{MNU}$ | = 8.6 × 10⁻⁶cm²/sec |
| $M_{EMS}$ | = 124.2 | $D_{EMS}$ | = 7.8 × 10⁻⁶cm²/sec |
| $M_{AcDMN}$ | = 132 | $D_{AcDMN}$ | = 7.6 × 10⁻⁶cm²/sec |
| $M_{NM}$ | = 116.1 | $D_{NM}$ | = 8.09 × 10⁻⁶cm²/sec |

-continued

| Molecular weight | | Diffusion coefficient | |
|---|---|---|---|
| $M_{NP}$ | = 100.2 | $D_{NP}$ | = 8.7 × 10⁻⁶cm²/sec |

The diffusion constants, D, and half lifetimes, $\tau_{\frac{1}{2}}$, were then used to generate the functional relationship between the average integrated concentration $C_{(r)}$ and r/R (relative distance from the center of the petri dish) employing equation II, supra. Plots of these data are illustrated in FIGS. 8–13.

With the help of these graphs and from the knowledge of the mutagenic zones, the minimal concentrations at which mutations were observed were calculated. The results for NG, MNU, EMS, AcDMN, NM and NP are presented in Tables 10–15. From the tables, it can be seen that the concentration of chemical at which mutation is observed, $C_{mut}$, for each of the chemicals varies within an order of magnitude. A mean value of $C_{mut}$ for each of the chemicals was obtained and summarized in Table 17. (90% confidence intervals are given as well).

TABLE 10

Figure 7:
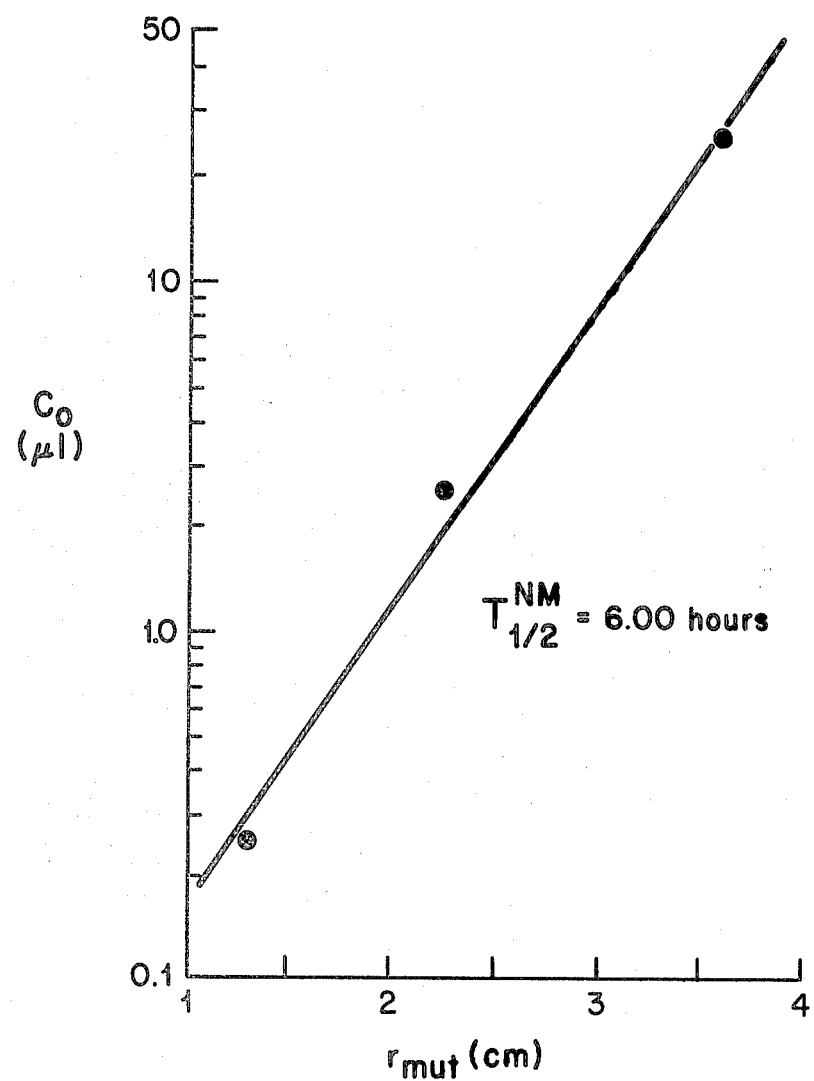
Figure 8:
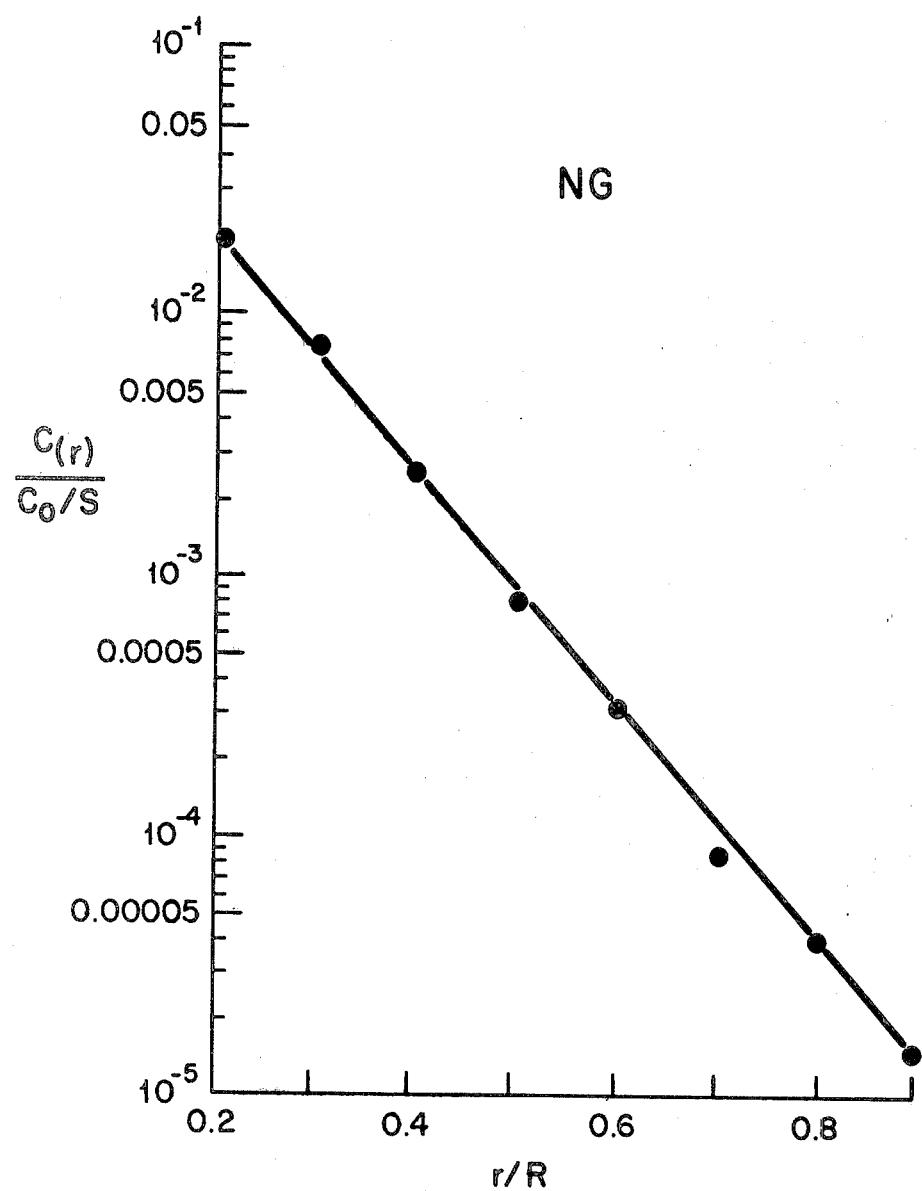
FIGS. 8-13 are plots of the time-integrated concentration profile versus the relative distance from the center of the petri dish for the mutagens tested.
Figure 9:
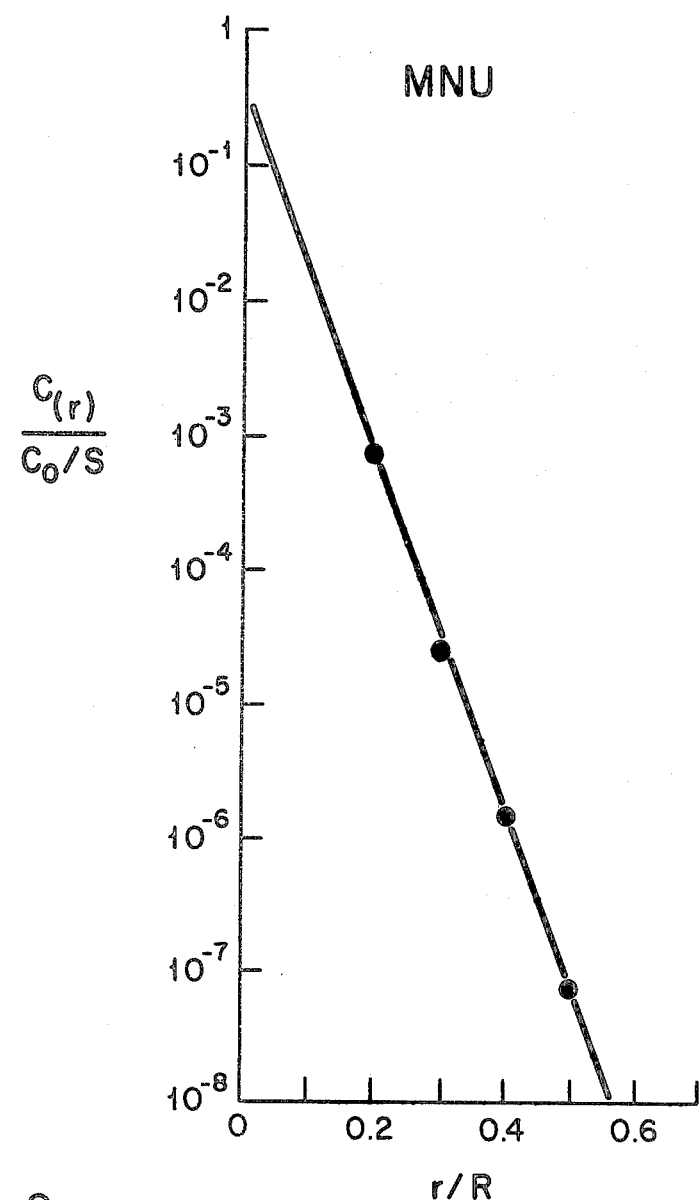
Figure 10:
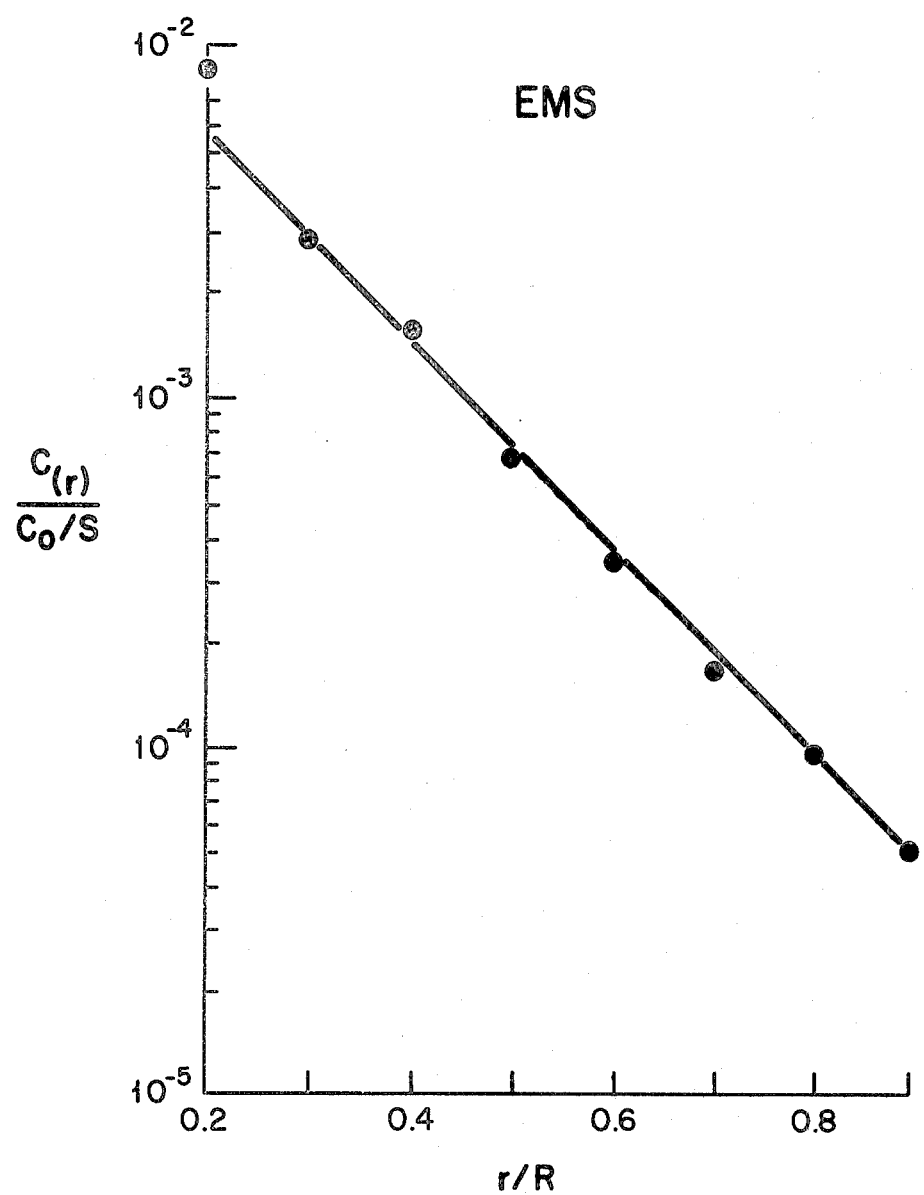
Figure 11:
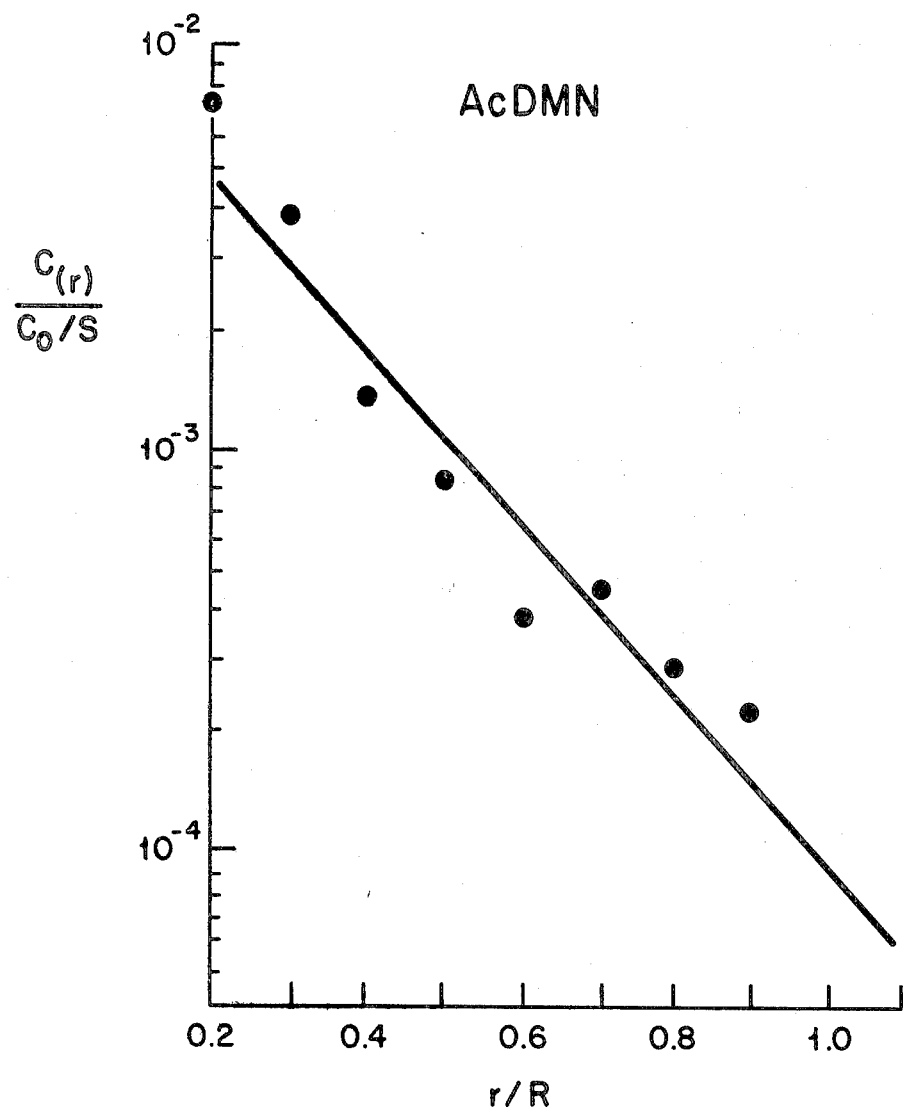
Figure 12:
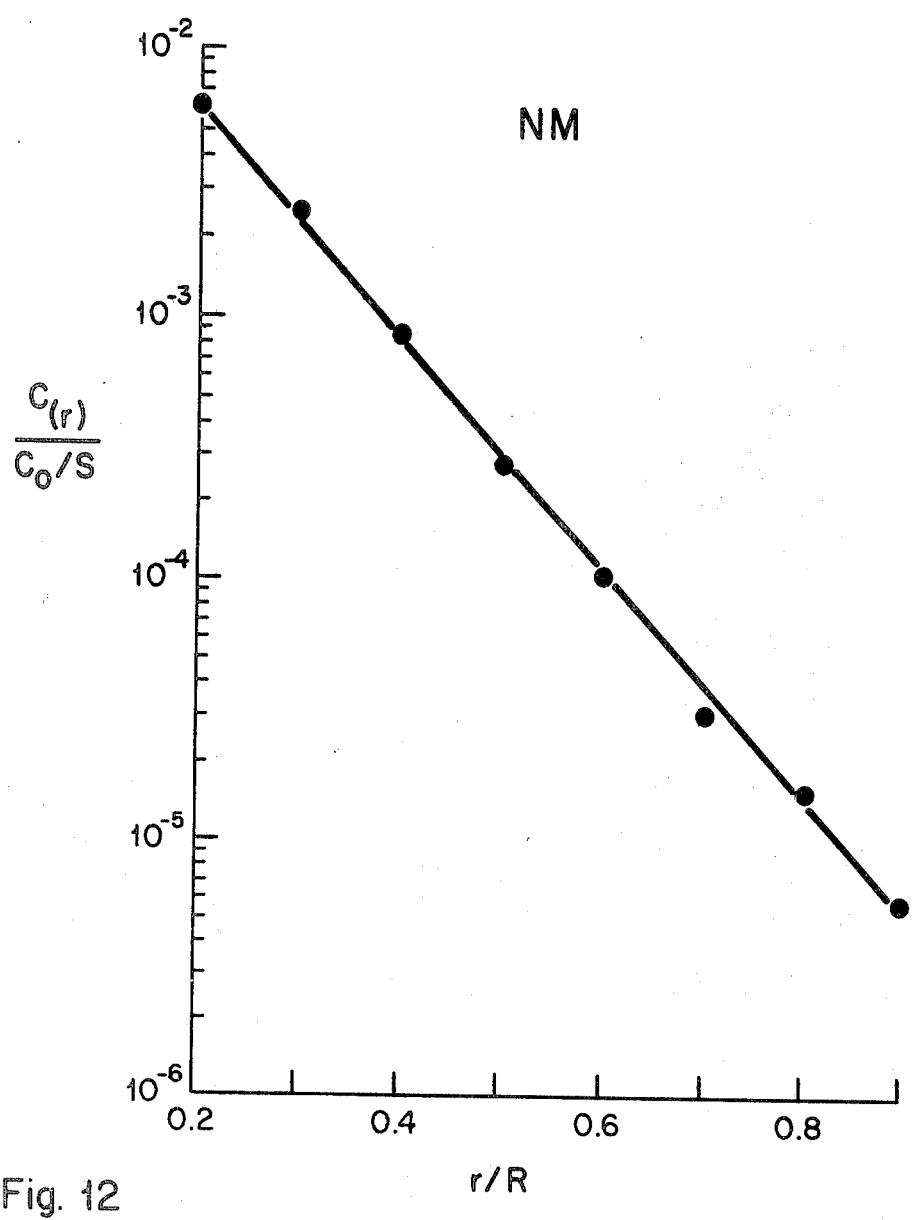
Figure 13:
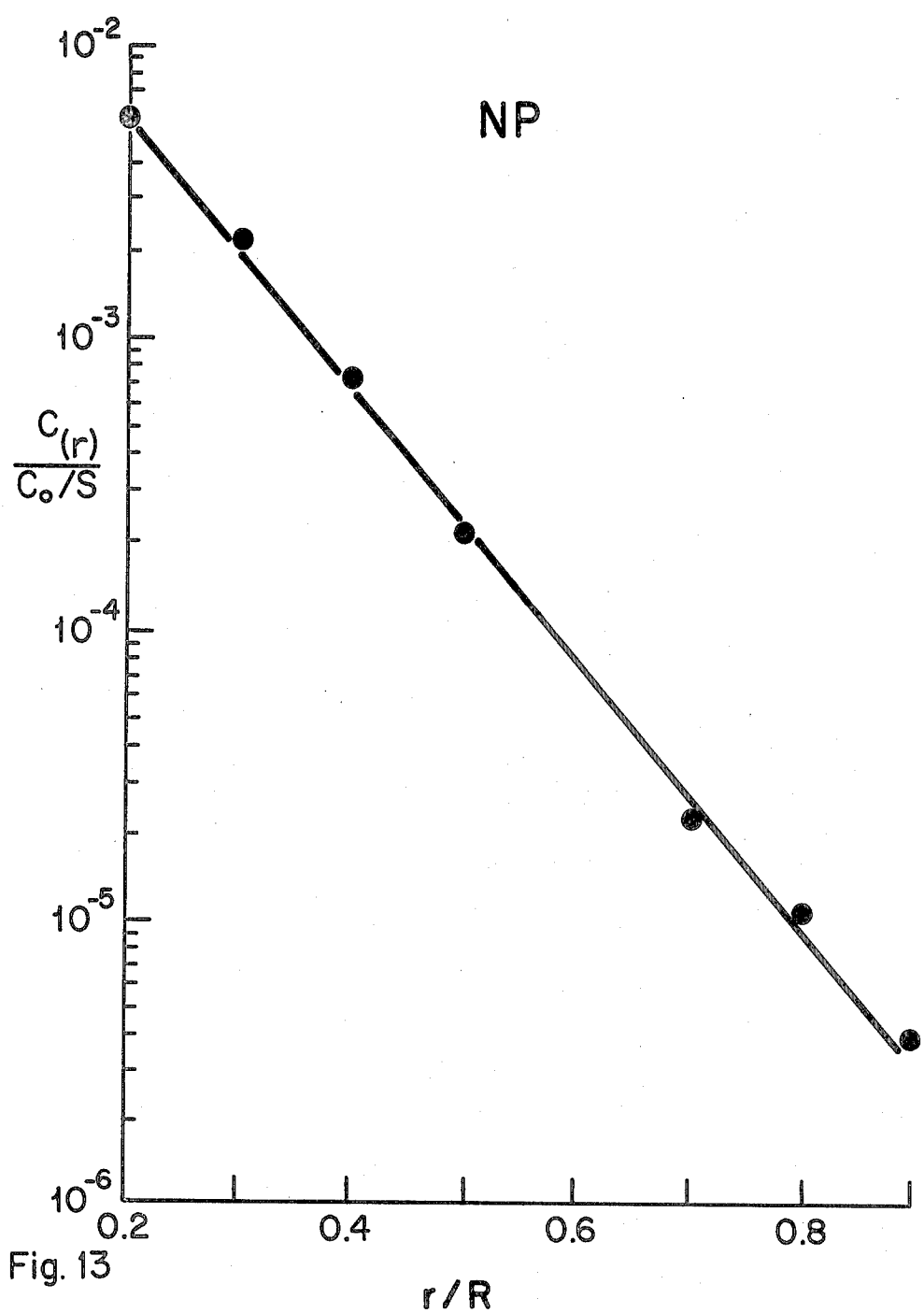

$C_{mut}$ for NG from Diffusion Experiments Using FIG. 7

| I $c_o$/s µg/ml | II $r_{mut}$(cm) | III $r_{mut}$/R$_{2.5}$ | IV *$C_{mut}$/$c_o$/s (From FIG. 7) | V *$C_{mut}$(µg/ml) |
|---|---|---|---|---|
| 221.04 | 2.22 ± 0.05 | 0.88 ± 0.02 | 1.5 × 10⁻⁵(1.2 × 10⁻⁵, 1.9 × 10⁻⁵) | 3.3 × 10⁻³(2.65 × 10⁻³, 4.19 × 10⁻³) |
| 110.52 | 1.98 ± 0.02 | 0.79 ± 0.01 | 4.1 × 10⁻⁵(3.75 × 10⁻⁵, 4.6 × 10⁻⁵) | 4.5 × 10⁻³(4.14 × 10⁻³, 5.08 × 10⁻³) |
| 22.1 | 1.55 ± 0.04 | 0.62 ± 0.01 | 2.4 × 10⁻⁴(2.02 × 10⁻⁴, 2.9 × 10⁻⁴) | 5.3 × 10⁻³(4.64 × 10⁻³, 6.4 × 10⁻³) |
| 2.21 | 0.88 ± 0.05 | 0.37 ± 0.02 | 3.2 × 10⁻³(2.6 × 10⁻³, 4.1 × 10⁻³) | 7.2 × 10⁻³(5.74 × 10⁻³, 9.06 × 10⁻³) |

Radius of Petri Dish: R = 2.5 cm
*The values outside the brackets are means and those inside define the range of one standard deviation.

TABLE 11

$C_{mut}$ for MNU from Diffusion Experiments Using FIG. 22

| I $c_o$/s µg/ml | II $r_{mut}$(cm) | III $r_{mut}$/R$_{4.25}$ | IV *$C_{mut}$/$c_o$/s (From FIG. 22) | V *$C_{mut}$(µg/ml) |
|---|---|---|---|---|
| 1606.1 | 1.12 ± 0.08 | 0.26 ± 0.02 | 0.94 × 10⁻⁴(0.5 × 10⁻⁴, 1.85 × 10⁻⁴) | 0.15(0.08, 0.29) |
| 803.05 | 0.94 ± 0.09 | 0.22 ± 0.02 | 0.38 × 10⁻³(0.17 × 10⁻³, 0.65 × 10⁻³) | 0.30(0.14, 0.52) |
| 160.6 | 0.70 ± 0.04 | 0.16 ± 0.009 | 0.20 × 10⁻²(0.15 × 10⁻², 0.27 × 10⁻²) | 0.32(0.24, 0.43) |
| 80.3 | 0.61 ± 0.06 | 0.14 ± 0.01 | 0.38 × 10⁻²(0.24 × 10⁻², 0.6 × 10⁻²) | 0.30(0.19, 0.48) |

Radius of Petri Dish: R = 4.25 cm
*The values outside the brackets are means and those inside define the range of one standard deviation.

TABLE 12

$C_{mut}$ for EMS from Diffusion Experiments Using FIG. 23

| *Volume µl | I $c_o$/s mg/ml | II $r_{mut}$(cm) | III $r_{mut}$/R$_{4.25}$ | IV Δ$C_{mut}$/$c_o$/s (From FIG. 23) | V Δ$C_{mut}$/µg/ml |
|---|---|---|---|---|---|
| 20 | 154.8 | 3.45 ± 0.16 | 0.81 ± 0.03 | 8.4 × 10⁻⁵(6.5 × 10⁻⁵, 10.7 × 10⁻⁵) | 13.00(10.06, 16.56) |
| 10 | 77.4 | 2.79 ± 0.07 | 0.65 ± 0.01 | 2.5 × 10⁻⁴(2.2 × 10⁻⁴, 2.75 × 10⁻⁴) | 19.3(17.02, 21.3) |
| 5 | 38.7 | 2.19 ± 0.10 | 0.51 ± 0.02 | 6.5 × 10⁻⁴(5.4 × 10⁻⁴, 7.7 × 10⁻⁴) | 25.1(20.8, 29.79) |
| 2 | 15.48 | 1.7 ± 0.08 | 0.40 ± 0.02 | 1.55 × 10⁻³(1.2 × 10⁻³, 1.65 × 10⁻³) | 23.99(19.35, 25.54) |

*d = 1.20492 Ref: P.W.C. Barnard and R.E. Robertson, Can. J. Chem. Vol. 39 (1961), p. 881.
Radius of Petri Dish: R = 4.25 cm
ΔThe values outside the brackets are means and those inside define the range of one standard deviation.

TABLE 13

$C_{mut}$ for AcDMN from Diffusion Experiments Using FIG. 24

| *Volume µl | I $c_o$/s* mg/ml | II $r_{mut}$(cm) | III $r_{mut}$/R$_{4.25}$ | IV Δ$C_{mut}$/$c_o$/s (From FIG. 24) | V Δ$C_{mut}$/µg/ml |
|---|---|---|---|---|---|
| 2 | 15.24 | 4.25 ± 0.00 | 1 ± 0.0 | 9 × 10⁻⁵ | 1.37 |
| 1 | 7.61 | 3.98 ± 0.16 | 0.94 ± 0.03 | 1.2 × 10⁻⁴(0.9 × 10⁻⁴, 7.4 × 10⁻⁴) | 0.91(0.69, 0.96) |
| 0.5 | 3.80 | 2.81 ± 0.14 | 0.66 ± 0.03 | 4.9 × 10⁻⁴(4.2 × 10⁻⁴, 5.7 × 10⁻⁴) | 1.8(1.6, 2.16) |

TABLE 13-continued

| | | | $C_{mut}$ for AcDMN from Diffusion Experiments Using FIG. 24 | |
|---|---|---|---|---|
| *Volume $\mu l$ | I $c_o/s$ mg/ml | II $r_{mut}$(cm) | III $r_{mut}/R_{4.25}$ | IV $^\Delta C_{mut}/c_o/s$ (From FIG. 24) | V $^\Delta C_{mut}/\mu g/ml$) |
| 0.2 | 1.52 | 1.66 ± 0.33 | 0.39 ± 0.07 | $1.9 \times 10^{-3}(1.3 \times 10^{-3}, 2.8 \times 10^{-3})$ | 2.8(1.95, 4.3) |

*d = 1.185 as measured by author.
R = 4.25 cm
$^\Delta$The values outside the brackets are means and those inside define the range of one standard deviation.

TABLE 14

| | | | $C_{mut}$ for NP from Diffusion Experiments Using FIG. 26 | |
|---|---|---|---|---|
| Volume $\Delta\mu l$ | I $c_o/s$ mg/ml | II $r_{mut}$(cm) | III $r_{mut}/R_{4.25}$ | IV *$C_{mut}/c_o/s$ (From FIG. 26) | V *$C_{mut}/\mu g/ml$ |
| 0.25 | 0.27 | 1.6 ± 0.18 | 0.38 ± 0.04 | $8.6 \times 10^{-4}(5.3 \times 10^{-4}, 12.7 \times 10^{-4})$ | 0.233(0.143, 0.344) |
| 2.5 | 2.71 | 2.5 ± 0.28 | 0.59 ± 0.06 | $8.6 \times 10^{-5}(4.6 \times 10^{-5}, 16.6 \times 10^{-5})$ | 0.233(0.125, 0.449) |
| 10 | 10.85 | 3.4 ± 0.32 | 0.80 ± 0.07 | $8.9 \times 10^{-6}(4.4 \times 10^{-6}, 9.6 \times 10^{-6})$ | 0.097(0.048, 0.212) |
| 25 | 27.1 | 3.7 ± 0.31 | 0.87 ± 0.07 | $4. \times 10^{-6}(3.01 \times 10^{-6}, 9.26 \times 10^{-6})$ | 0.108(0.082, 0.25) |

$\Delta$d = 1.08 Ref: Aldrich Catalogue
Radius of Petri Dish: R = 4.25 cm
*The values outside the brackets are means and those inside define the range of one standard deviation.

TABLE 15

| | | | $C_{mut}$ for NM from Diffusion Experiments Using FIG. 25 | |
|---|---|---|---|---|
| Volume $\Delta\mu l$ | I $c_o/s$ mg/ml | II $r_{mut}$(cm) | III $r_{mut}/R_{4.25}$ | IV *$C_{mut}/c_o/s$ (From FIG. 25) | V *$C_{mut}/\mu g/ml$ |
| 0.25 | 0.29 | 1.31 ± 0.1 | 0.3 ± 0.02 | $2.2 \times 10^{-3}(1.5 \times 10^{-3}, 2.7 \times 10^{-3})$ | 0.64(0.436, 0.785) |
| 2.5 | 0.91 | 2.25 ± 0.12 | 0.52 ± 0.02 | $2.4 \times 10^{-4}(1.6 \times 10^{-4}, 3.1 \times 10^{-4})$ | 0.699(0.465, 0.902) |
| 25 | 29.1 | 3.6 ± 0.3 | 0.84 ± 0.07 | $9.5 \times 10^{-6}(4.1 \times 10^{-6}, 17.37 \times 10^{-6})$ | 0.276(0.119, 0.505) |

$\Delta$d = 1.164 as determined by author.
Radius of Petri Dish: R = 4.25 cm
*The values outside the brackets are means and those inside define the range of one standard deviation.

For each of the homogeneous bioassays, a plot was constructed of the number of colonies produced by incubation of the bacteria with different concentrations of mutagen. Each gave a straight line. The value of the minimum mutagenic concentration ($C_{mut}^{hom}$) was obtained from the intercept of the straight line with the abscissa. This was taken as the lowest concentration of the chemical at which mutagenicity occurred. For NG, the minimal mutagenic concentration was calculated to be:

$$C_{mut}^{hom} = \frac{0.42 \ \mu g/ml \times 0.2ml}{7 \ ml \ agar} = 12 \times 10^{-3} \mu g/ml.$$

In the same manner, $C_{mut}^{hom}$ for the other chemicals was determined. The results, with 90% confidence intervals, are presented in Table 16.

TABLE 16

| Threshold Values Obtained from Different Methods with 90% Confidence Intervals | | | |
|---|---|---|---|
| | $^\Delta C_{mut}(\mu g/ml)$ | $C_{mut}^{hom}$ | $\tau_{\frac{1}{2}}$ hrs |
| NG | 0.0051(0.0033, 0.0081) | 0.012 ± 0.069 | 2.25 |
| MN | 0.27(0.13, 0.45) | 0.116 ± 2.52 | 0.628 |
| AcDMN | 1.7(1.07, 3.53) | 1.01 ± 1.48 | 34.15 |
| EMS | 20.3(13.17, 26.97) | 16.85 ± 10.85 | 14.5 |
| NM* | 0.54(0.23, 0.80) | 0.7 ± 3.6 | 6.0 |
| NP* | 0.17(0.10, 0.37) | 0.58 ± 4.8 | 5.10 |

*Need metabolic activation.
$^\Delta$The values outside the brackets are means and those inside define the range of 90% confidence intervals.

The effect of the initial number of bacteria on the dimensions of the mutagenic zones was examined for NG and EMS. The results are presented in Tables 17 and 18, respectively.

TABLE 17

| The Effect of Bacteria Number on the Mutagenic and Toxic Zones | | | |
|---|---|---|---|
| Initial # of Bacteria | *–HIS $r_{mut}$(cm) | *–HIS $r_{tox}$(cm) | *+HIS $r_{tox}$(cm) |
| $6.4 \times 10^8$ | 2.26 ± 0.05 | 1.06 ± 0.06 | 1.1 ± 0.05 |
| $6.4 \times 10^7$ | 2.30 ± 0.04 | 1.22 ± 0.02 | 1.17 ± 0.04 |
| $6.4 \times 10^6$ | 2.25 ± 0.04 | 1.39 ± 0.04 | 1.31 ± 0.07 |
| $6.4 \times 10^5$ | 2.24 ± 0.04 | 1.53 ± 0.07 | 1.35 ± 0.04 |
| $6.4 \times 10^4$ | 2.13 ± 0.02 | 1.63 ± 0.05 | 1.40 ± 0.05 |

The Mutagen: NG - 25 $\mu l$ of 1000 $\mu g/ml$ per disc
The Strain: S. typhimurium TA 1535
Size of Petri Dish: R = 4.25 cm
*$r_{mut}$ and $r_{tox}$ are means of 6 measurements.

TABLE 18

| The Effect of Bacteria Number on the Mutagenic and Toxic Zones | | | |
|---|---|---|---|
| Initial # of Bacteria | *–HIS $r_{mut}$(cm) | *–HIS $r_{tox}$(cm) | *+HIS $r_{tox}$(cm) |
| $3.1 \times 10^9$ | 3.6 ± 0.27 | 1.48 ± 0.08 | 1.28 ± 0.03 |
| $3.1 \times 10^8$ | 3.56 ± 0.25 | 1.16 ± 0.03 | 1.85 ± 0.05 |
| $3.1 \times 10^7$ | 3.6 ± 0.1 | 2.15 ± 0.22 | 2.12 ± 0.02 |
| $3.1 \times 10^6$ | 3.5 ± 0.24 | 2.48 ± 0.19 | 2.42 ± 0.07 |

The Mutagen: EMS - 25 $\mu l$ per disc
The Strain: S. typhimurium TA 1535
Size of Petri Dish: 4.25 cm
*$r_{mut}$ and $r_{tox}$ are means of 6 measurements.

The dimensions of the mutagenic zone were the same for assay plates containing different initial numbers of bacteria, although the size and number of the colonies around the mutagenic edge were different for different concentration of bacteria. Thus, the mutagenic zone appears to be independent of the initial bacterial concentration, at least within the 10,000-fold dilution of the organism.

EXAMPLE II

The tester strain employed for detecting frame-shift mutagens was TA-1538. The procedures were substantially the same as those of Example 1.

The chemicals tested were ICR-191 and 2-AAF (a-acetyl amino fluorene) which required the metabolic activation previously described.

The radii of mutagenic zones formed by different concentrations of ICR-191 are given below:

| $C_o$(mg/ml) | $r_{mut}$(cm) | |
|---|---|---|
| 1000 | 1.52 | |
| 100 | 1.16 | $M = 403.1$  $D = 4.34 \times 10^{-6} cm^2/sec$ |
| 10 | 0.73 | $\tau_{\frac{1}{2}} = 2.09$ hrs. |

The radii of mutagenic zones formed by different concentrations of 2-AAF are given below:

| $C_o$(mg/ml) | $r_{mut}$(cm) | |
|---|---|---|
| 1000 | 1.12 | $M = 223.3$ |
| 100 | 0.85 | $D = 5.84 \times 10^{-6} cm^2/sec$ |
| | | $\tau_{\frac{1}{2}} = 0.446$ hrs. |

INDUSTRIAL APPLICABILITY

The invention has industrial applicability in the testing of compounds and other agents for their mutagenicity.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A bioassay for determining the degree of mutagenicity of an agent, comprising:
    a. forming a culture of living cells, said cells being a tester strain for mutagenesis;
    b. applying a spot of test agent in known concentration to said culture whereby said test agent diffuses outwardly from said spot to form a ring-shaped mutagenic band in which viable mutant cells are produced, said ring-shaped mutagenic band being concentric to the spot of test agent;
    c. measuring the length of a radius from said spot to said ring-shaped mutagenic band; and,
    d. employing the length of said radius to determine the degree of mutagenicity of said agent.

2. A bioassay of claim 1 wherein said test agent comprises a water-soluble chemical substance.

3. A bioassay of claim 2 wherein said radius extends from the center of said spot of test agent to the outside perimeter of said ring-shaped mutant band.

4. A bioassay of claims 1 or 3 wherein said living cells comprise human cells.

5. A bioassay of claims 1 or 3 wherein said living cells comprise bacterial cells.

6. A method for determining the half-lifetime ($\tau_{\frac{1}{2}}$) of a potential mutagenic agent in a cell culture environment, comprising:
    a. forming a culture of living cells, said cells being a tester strain for mutagenesis;
    b. applying a spot of test agent in known concentration to said culture whereby said test agent diffuses outwardly from said spot to form a ring-shaped mutagenic band in which viable mutant cells are produced, said ring-shaped mutagenic band being concentric to said spot of test agent;
    c. measuring the length of a radius extending from the center of said spot to the outer perimeter of said ring-shaped mutagenic band;
    d. repeating steps a-c a sufficient number of times with different initial concentrations of test agent to allow a plot to be constructed relating the initial concentration of agent to the length of radius measured;
    e. constructing a plot relating the initial concentration to the length of the radius measured for a plurality of initial concentrations; and,
    f. determining the slope of said plot as an indication of the half-lifetime of said agent.

* * * * *